United States Patent
Leschinsky

(10) Patent No.: US 9,801,780 B2
(45) Date of Patent: Oct. 31, 2017

(54) METHODS AND DEVICES FOR REMOTE ISCHEMIC CONDITIONING VIA PARTIAL LIMB OCCLUSION

(71) Applicant: Infarct Reduction Technologies Inc., Waldwick, NJ (US)

(72) Inventor: Boris Leschinsky, Mahwah, NJ (US)

(73) Assignee: LifeCuff Technologies Inc., Waldwick, NJ (US)

( * ) Notice: Subject to any disclaimer, the term of this patent is extended or adjusted under 35 U.S.C. 154(b) by 435 days.

(21) Appl. No.: 14/661,988

(22) Filed: Mar. 18, 2015

(65) Prior Publication Data

US 2015/0190301 A1    Jul. 9, 2015

Related U.S. Application Data

(63) Continuation-in-part of application No. 14/305,032, filed on Jun. 16, 2014, now Pat. No. 9,610,213, which
(Continued)

(51) Int. Cl.
*A61B 5/022* (2006.01)
*A61H 9/00* (2006.01)
(Continued)

(52) U.S. Cl.
CPC ....... *A61H 9/0092* (2013.01); *A61B 5/02208* (2013.01); *A61B 5/02225* (2013.01); *A61B 5/02233* (2013.01); *A61B 17/12109* (2013.01); *A61B 17/12136* (2013.01); *A61B 17/135* (2013.01); *A61B 17/1355* (2013.01); *A61B 2017/00199* (2013.01);
(Continued)

(58) Field of Classification Search
CPC .......... A61H 9/0092; A61H 2201/5035; A61H 2201/5038; A61H 2201/5071; A61H 2205/06; A61H 2205/10; A61H 2230/30; A61B 5/02208; A61B 5/02225; A61B 5/02233; A61B 17/12109; A61B 17/12136; A61B 17/135; A61B 17/1355; A61B 2017/00199
USPC .................................................. 600/490–499
See application file for complete search history.

(56) References Cited

U.S. PATENT DOCUMENTS

| | | | | |
|---|---|---|---|---|
| 4,664,651 A | * | 5/1987 | Weinshenker | ....... A61B 17/135 600/490 |
| 4,690,151 A | * | 9/1987 | Utsunomiya | ...... A61B 5/02208 600/495 |

(Continued)

OTHER PUBLICATIONS

Berry B.E., Pinard A. E. Assessing Tissue Oxygenation. Critical Care Nurse vol. 22, No. 3, Jun. 2002, pp. 22-40.
(Continued)

*Primary Examiner* — Navin Natnithithadha
(74) *Attorney, Agent, or Firm* — Boris Leschinsky

(57) ABSTRACT

Single- or dual-bladder devices for automated delivery of remote ischemic conditioning treatment via partial limb occlusion involve various methods of operating the cuff in which partial or full limb occlusion is achieved during the periods of cuff inflation. Achieving clinical benefits of remote ischemic conditioning without extended cessation of limb blood flow are advantageous due to lower required cuff pressure and reduced risk of clot formation in the limb vasculature.

22 Claims, 5 Drawing Sheets

Related U.S. Application Data is a continuation of application No. 13/362,039, filed on Jan. 31, 2012, now Pat. No. 8,753,283, which is a continuation of application No. 12/820,273, filed on Jun. 22, 2010, now Pat. No. 8,114,026.

(60) Provisional application No. 61/219,536, filed on Jun. 23, 2009, provisional application No. 61/256,038, filed on Oct. 29, 2009.

(51) Int. Cl.
 A61B 17/135 (2006.01)
 A61B 17/12 (2006.01)
 A61B 17/00 (2006.01)

(52) U.S. Cl.
 CPC ............ A61H 2201/5035 (2013.01); A61H 2201/5038 (2013.01); A61H 2201/5071 (2013.01); A61H 2205/06 (2013.01); A61H 2205/10 (2013.01); A61H 2230/30 (2013.01)

(56) References Cited

U.S. PATENT DOCUMENTS

| | | | | |
|---|---|---|---|---|
| 5,072,736 A * | 12/1991 | Ogawa | A61B 8/06 | 600/454 |
| 5,267,565 A * | 12/1993 | Beard | A61B 5/0285 | 600/454 |
| 5,687,732 A * | 11/1997 | Inagaki | A61B 5/02233 | 600/485 |
| 5,733,304 A * | 3/1998 | Spence | A61B 17/135 | 606/203 |
| 5,842,996 A * | 12/1998 | Gruenfeld | A61B 17/135 | 600/490 |
| 6,152,880 A * | 11/2000 | Okada | A61B 5/0255 | 600/485 |
| 6,152,881 A * | 11/2000 | Raines | A61B 5/02007 | 600/504 |
| 6,210,423 B1 * | 4/2001 | Kim | A61B 17/1325 | 128/898 |
| 6,251,080 B1 * | 6/2001 | Henkin | A61B 5/02233 | 600/490 |
| 6,344,025 B1 * | 2/2002 | Inagaki | A61B 5/0002 | 600/485 |
| 6,361,548 B1 * | 3/2002 | McEwen | A61B 17/132 | 606/201 |
| 6,478,745 B2 * | 11/2002 | Nakagawa | A61B 5/021 | 600/499 |
| 6,682,547 B2 * | 1/2004 | McEwen | A61B 17/135 | 356/425 |
| 6,858,012 B2 * | 2/2005 | Burns | A61B 5/0205 | 600/481 |
| 6,962,599 B2 * | 11/2005 | Hui | A61G 7/05776 | 606/202 |
| 7,048,702 B2 * | 5/2006 | Hui | A61H 9/0078 | 601/150 |
| 7,314,478 B2 * | 1/2008 | Hui | A61G 7/05776 | 606/202 |
| 7,331,977 B2 * | 2/2008 | McEwen | A61B 17/135 | 606/202 |
| 7,374,540 B2 * | 5/2008 | Schnall | A61B 5/0295 | 600/310 |
| 7,384,425 B2 * | 6/2008 | McEwen | A61B 17/132 | 600/495 |
| 7,390,303 B2 * | 6/2008 | Dafni | A61B 5/02007 | 600/485 |
| 7,717,855 B2 | 5/2010 | Caldarone | | |
| 7,758,607 B2 * | 7/2010 | McEwen | A61B 17/135 | 606/202 |
| 7,771,453 B2 * | 8/2010 | McEwen | A61B 17/1355 | 600/490 |
| 7,780,698 B2 * | 8/2010 | McEwen | A61B 17/135 | 606/203 |
| 7,909,849 B2 * | 3/2011 | McEwen | A61B 17/132 | 600/495 |
| 8,114,026 B2 | 2/2012 | Leschinsky | | |
| 8,123,694 B2 * | 2/2012 | Kinsley | A61B 5/02141 | 600/485 |
| 8,137,378 B2 * | 3/2012 | McEwen | A61B 17/1322 | 606/203 |
| 8,246,548 B2 | 8/2012 | Naghavi | | |
| 8,753,283 B2 | 6/2014 | Leschinsky | | |
| 8,764,789 B2 | 7/2014 | Ganske | | |
| 8,790,266 B2 | 7/2014 | Caldarone | | |
| 8,795,323 B2 | 8/2014 | Leschinsky | | |
| 8,911,469 B2 | 12/2014 | Raheman | | |
| 8,974,491 B2 | 3/2015 | Leschinsky | | |
| 8,986,342 B2 | 3/2015 | Naghavi | | |
| 9,119,759 B2 * | 9/2015 | Caldarone | A61H 9/0078 | |
| 9,119,761 B2 * | 9/2015 | Caldarone | A61H 9/0078 | |
| 9,205,019 B2 * | 12/2015 | Ganske | A61B 17/1325 | |
| 9,393,025 B2 * | 7/2016 | Caldarone | A61B 17/132 | |
| 9,610,213 B2 * | 4/2017 | Leschinsky | A61B 5/02208 | |
| 2001/0029389 A1 * | 10/2001 | Kim | A61B 17/1325 | 606/203 |
| 2002/0147404 A1 * | 10/2002 | Kato | A61B 5/681 | 600/503 |
| 2003/0065270 A1 * | 4/2003 | Raines | A61B 5/02007 | 600/504 |
| 2005/0177078 A1 * | 8/2005 | Loeb | A61H 99/00 | 601/152 |
| 2007/0005106 A1 * | 1/2007 | Adducci | A61B 17/135 | 606/202 |
| 2007/0160645 A1 | 7/2007 | Vinten-Johansen | | |
| 2008/0081963 A1 * | 4/2008 | Naghavi | A61B 5/01 | 600/301 |
| 2008/0139949 A1 | 6/2008 | Caldarone | | |
| 2009/0137884 A1 | 5/2009 | Naghavi | | |
| 2009/0287069 A1 | 11/2009 | Naghavi | | |
| 2009/0318818 A1 * | 12/2009 | Whitaker | A61B 5/02233 | 600/495 |
| 2010/0105993 A1 | 4/2010 | Naghavi | | |
| 2010/0160799 A1 | 6/2010 | Caldarone | | |
| 2010/0185220 A1 | 7/2010 | Naghavi | | |
| 2010/0292619 A1 * | 11/2010 | Redington | A61H 9/0078 | 601/84 |
| 2010/0305607 A1 | 12/2010 | Caldarone | | |
| 2010/0324429 A1 | 12/2010 | Leschinsky | | |
| 2011/0190807 A1 | 8/2011 | Redington | | |
| 2011/0208099 A1 | 8/2011 | Naghavi | | |
| 2011/0238107 A1 * | 9/2011 | Raheman | A61B 5/412 | 606/202 |
| 2011/0240043 A1 | 10/2011 | Redington | | |
| 2011/0251635 A1 | 10/2011 | Caldarone | | |
| 2011/0319732 A1 | 12/2011 | Naghavi | | |
| 2012/0130419 A1 | 5/2012 | Leschinsky | | |
| 2012/0265240 A1 | 10/2012 | Ganske | | |
| 2012/0277789 A1 | 11/2012 | Caldarone | | |
| 2013/0184745 A1 | 7/2013 | Leschinsky | | |
| 2014/0200464 A1 | 7/2014 | Webster | | |
| 2014/0296756 A1 | 10/2014 | Ganske | | |
| 2014/0296757 A1 | 10/2014 | Leschinsky | | |

OTHER PUBLICATIONS

Walsh SR, Tang T, Sadat U, Dutka DP, Gaunt ME. Cardioprotection by remote ischaemic preconditioning. Br J Anaesthesia 99;5:611-616, 2007.

Hausenloy DJ, Yellon DM. Remote ischaemic preconditioning: underlying mechanisms and clinical application. Cardiovasc Res 79:377-386, 2008.

Tapuria N, Kumar Y, Habib MM, Amara MA, Seifalian AM, Davidson BR. Remote ischemic preconditioning: a novel protective method from ischemia reperfusion injury—a review. J Surg Res 150;2:304-330, 2008.

Birnbaum Y, Hale SL, Kloner RA. Ischemic preconditioning at a distance. Circulation, 96:1641-1646, 1997.

Kharbanda RK, Nielsen TT, Redington AN. Translation of remote ischaemic preconditioning into clinical practice. Lancet 374:1557-1565, 2009.

(56) References Cited

OTHER PUBLICATIONS

Xiong J, Liao X, Xue FS, Yuan YJ, Wang Q, Liu JH. Remote ischemia conditioning—an endogenous cardioprotective strategy from outside the heart. Chin Med J 124(14):2209-2215, 2011.

Szijártó A, Czigány Z, Turóczi Z, Harsányi L. Remote ischemic preconditioning—a simple, low-risk method to decrease ischemic reperfusion injury: models, protocols and mechanistic background. A review. J Surg Res. 178, 797-806, 2012.

Lim SY, Hausenloy DJ. Remote ischemic conditioning: from bench to bedside. Front Physio 3:27, 2012.

Heusch G, Bøtker HE, Przyklenk K, Redington A, Yellon D. Remote ischemic conditioning. J Am Coll Cardiol 65(2):177-195, 2015.

Sivaraman V, Pickard JMJ, Hausenloy DJ. Remote ischaemic conditioning: cardiac protection from afar. Anaesthesia 2015. First published online Feb. 26, 2015.

\* cited by examiner

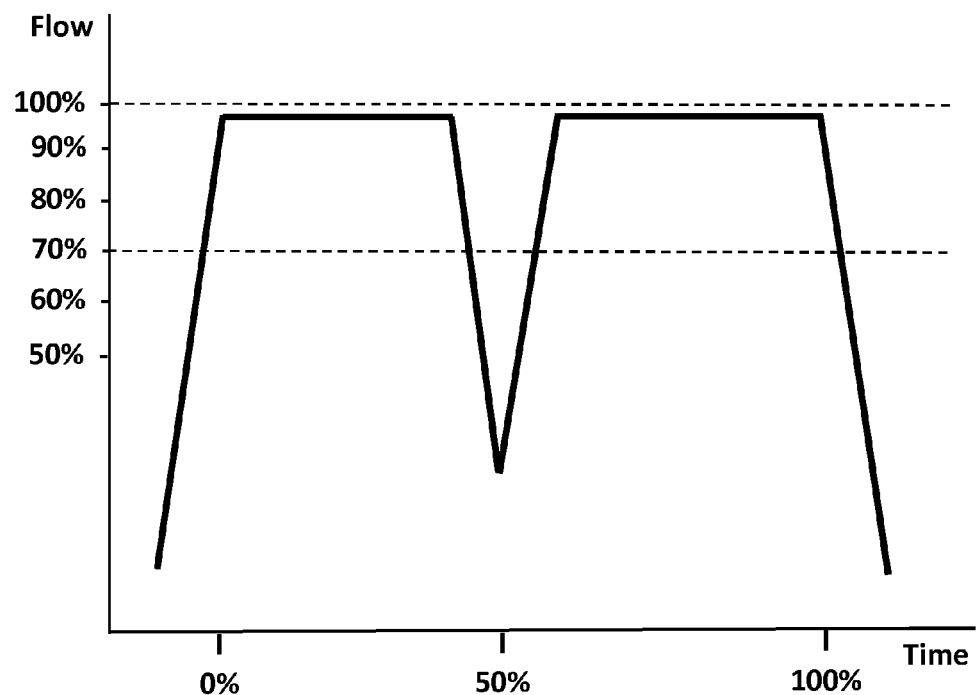
FIG. 9 |----------------Cuff Deflation Period--------------|
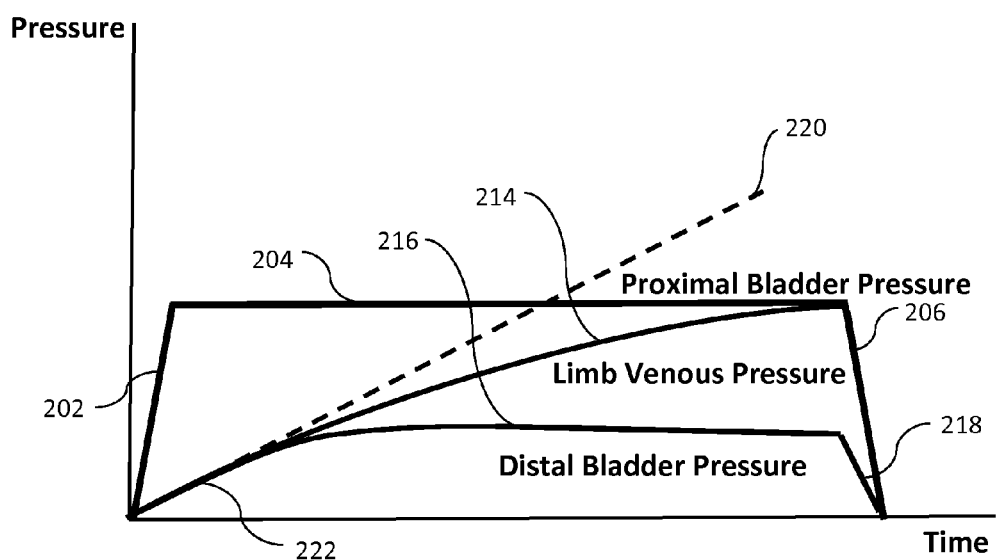
FIG. 10

METHODS AND DEVICES FOR REMOTE ISCHEMIC CONDITIONING VIA PARTIAL LIMB OCCLUSION

CROSS-REFERENCE DATA

This patent application is a continuation-in-part of my co-pending U.S. patent application Ser. No. 14/305,032 filed Jun. 16, 2014 entitled "AUTOMATIC DEVICES FOR REMOTE ISCHEMIC PRECONDITIONING"; which is in turn a continuation of my U.S. patent application Ser. No. 13/362,039 filed Jan. 31, 2012 with the same title, now U.S. Pat. No. 8,753,283; which in turn is a continuation of the U.S. patent application Ser. No. 12/820,273 entitled "METHODS AND DEVICES FOR REMOTE ISCHEMIC PRECONDITIONING AND NEAR-CONTINUOUS BLOOD PRESSURE MONITORING" filed Jun. 22, 2010, now U.S. Pat. No. 8,114,026; which in turn claims a priority benefit from the U.S. Provisional Patent Application No. 61/219,536 filed Jun. 23, 2009 entitled "BLOOD PRESSURE CUFF INCORPORATING A PRECONDITIONING DEVICE" and the U.S. Provisional Patent Application No. 61/256,038 filed Oct. 29, 2009 entitled "PRECONDITIONING DEVICES FOR USE IN AMI AND PERCUTANEOUS INTERVENTION SETTINGS", all above listed documents incorporated herein by reference in their respective entireties.

BACKGROUND OF THE INVENTION

The present invention relates generally to methods and devices for delivery of a remote ischemic conditioning treatment. Such treatment may be used to achieve a variety of clinical benefits including for example a reduction of a harmful effect of ischemia and reperfusion injury of an organ, such as reducing of infarct size in a heart after acute myocardial infarction or reducing the extent of neuronal damage after a stroke. Other clinical benefits of remote ischemic conditioning may also be sought by using the devices and methods of the present invention—such as reducing inflammation, improving tissue survival, etc. as described in my previous patents as well as in related literature. More particularly, the invention describes methods and devices configured to deliver remote ischemic conditioning using partial limb occlusion.

The term "remote ischemic conditioning" is used herein to describe a non-invasive treatment generally consisting of a series of brief sub-lethal episodes of ischemia alternating with reperfusion applied to a limb of a subject (such as an upper arm or a thigh) in order to induce ischemic tolerance, reduce harmful effects of ischemia-reperfusion injury or to achieve other clinical benefits. Other terms used in the literature to describe this treatment include "remote ischemic postconditioning", "remote ischemic perconditioning", and "remote ischemic preconditioning". For the purposes of this description, all such treatments are contemplated in this invention and are described using the general term "remote ischemic conditioning" whether the treatment is done prior to, during, or after the ischemia as well as prior to, during, or after restoration of blood flow to the ischemic organ or tissue bed.

An inflatable cuff placed over a limb of a subject may be conveniently used to deliver remote ischemic conditioning. Such cuffs are ubiquitously used for measurement of a subject's blood pressure or as pneumatic tourniquets and therefore are familiar not only to medical professionals but also to the general public.

U.S. Pat. No. 7,717,855 to Caldarone et al. is incorporated herein by reference in its entirety and discloses one example of an automatic device configured to deliver remote ischemic conditioning by periodic inflation and deflation of an inflatable cuff placed over a limb of a subject. Blood flow through the limb is entirely stopped for at least about one minute (and typically about 5 minutes) by inflating the cuff to a predetermined set pressure above the systolic blood pressure of the subject. One sited example of such set pressure is 200 mmHg. Upon deflation of the cuff, blood flow is restored to its unrestricted level for the entire duration of cuff deflation.

The approach described in the '855 patent has a limitation in that inflating the cuff to such high pressure for extended periods of time may cause pain and discomfort to the subject. In some subjects, prolonged cessation of blood flow may also cause clot formation and increase the risk of thromboembolism, especially when the limb of choice is a leg and not the upper arm.

There is a need therefore for a more gentle approach in delivering remote ischemic conditioning treatment aimed at achieving effective results at lower cuff inflation pressures and minimizing the risk of thrombus formation resulting from such treatment.

SUMMARY OF THE INVENTION

It is an object of the present invention to provide novel methods and devices for delivery of remote ischemic conditioning treatment while minimizing pain and discomfort of the subject.

It is a further object of the present invention to provide novel methods and devices for delivery of remote ischemic conditioning treatment while minimizing the risk of clot formation and subsequent thromboembolism.

According to one aspect of the invention, complete occlusion of the limb and cessation of the blood flow is not necessary for achieving effective remote conditioning benefit. Partial occlusion may be used for the purpose of causing sufficiently strong ischemic stress to trigger the onset of remote ischemic conditioning protection. The terms "partial occlusion" and "partial reduction in blood flow" are used interchangeably throughout this specification.

In other aspects of the present invention, complete restoration of full blood flow in the limb during the periods of cuff deflation may also not be necessary. Sufficient increase in blood flow but not complete restoration thereof to the unrestricted level may be used for the purposes of achieving clinically useful remote ischemic conditioning benefits.

In general terms, remote ischemic conditioning effect is triggered by alternating periods or ischemia and reperfusion. Prior art describes remote ischemic conditioning treatment as several treatment cycles, each cycle including a period of limb ischemia caused by complete occlusion of blood flow in the limb for about one minute or more (typically 5 minutes) followed by a period of reperfusion when blood flow in the limb is restored entirely to its unrestricted state. This is achieved by first inflating a cuff placed over the limb to a pressure exceeding systolic blood pressure of the subject during the occlusion period and then deflating the cuff entirely to restore normal circulation during the reperfusion period.

The present invention recognizes the fact that intermittent complete occlusion of the limb triggers a certain level of temporary oxygen deprivation for the limb tissue, which in turn causes a corresponding degree of ischemic stress, which then leads to a desirable neuronal and humoral internal signaling and ultimately triggers a systemic release of various protective substances and activation of other protective mechanisms cumulatively defining the notion of the remote ischemic conditioning effect.

Importantly, achieving a minimally effective threshold of ischemic stress sufficient for triggering the remote ischemic conditioning effect may not require complete cessation of blood flow according to the present invention. Sufficient ischemia may be caused by only a partial but deep enough reduction of blood flow in the limb. Incomplete occlusion of blood flow, at least during a portion of the cuff inflation period may offer a number of significant advantages as compared with complete occlusion of blood flow described in the prior art. One of these advantages is a reduced level of cuff pressure required to derive the benefits of remote ischemic conditioning. Another advantage is a reduced risk of clot formation as some blood flow may still be allowed to get through to the limb tissue so the areas and durations of blood stasis may be reduced or entirely avoided.

The term "ischemic stress" is used herein to describe a minimum state of underperfusion of the limb tissue, which triggers the onset of remote ischemic conditioning mechanisms. Subsequently, the invention defines a minimally effective reduction of blood flow in the limb to achieve that threshold level of ischemic stress. The invention also teaches that relieving the ischemic stress may be achieved by increasing blood flow using for example at least some degree of deflation of the cuff from the cuff pressure necessary to achieve ischemic stress. Importantly, the cuff may not have to be deflated entirely. At least partial restoration of blood flow and at least some increase in limb oxygenation may be sufficient to relieve the ischemic stress necessary for the purposes of remote ischemic conditioning treatment.

The term "inflating" is used to describe increasing cuff pressure from a current level to a certain target level. The term "deflating" is used to describe decreasing cuff pressure from a current level to a certain target level. The term "cuff inflation period" defines the period of time following initial cuff inflation and starting at the point of cuff pressure reaching the target level needed to induce ischemic stress—and lasting for a predetermined duration after which the cuff is deflated to relieve ischemic stress. The term "cuff deflation period" defines the duration of time starting at the point when the cuff is first deflated to a pressure sufficiently low to relieve ischemic stress—and lasting until the next cuff inflation period or for a predetermined duration of time.

The method of the invention therefore describes the steps of delivering remote ischemic conditioning treatment as alternating:
 a. limb compression to reduce but not necessarily completely occlude blood flow to achieve or exceed a predefined ischemic stress threshold with
 b. limb reperfusion when blood flow is increased to at least a level sufficient to relieve the ischemic stress.

According to other embodiments of the invention, a method of performing remote ischemic conditioning may comprise the steps of:
 a. causing an ischemic stress in a limb of a subject by at least partially reducing blood flow therethrough for a period of at least about one minute, while avoiding complete occlusion of the limb lasting about one minute or longer,
 b. relieving the ischemic stress by increasing blood flow in the limb, and
 c. repeating steps (a) and (b).

Another yet method of performing remote ischemic conditioning may comprise the steps of:
 a. inflating a cuff placed over a limb of a subject to at least partially reduce blood flow therein and cause an ischemic stress therein reaching or exceeding a predetermined ischemic stress threshold for a period of at least about one minute, while avoiding inflating the cuff to cause complete occlusion of the limb for a period of about one minute or longer,
 b. deflating the cuff to increase the blood flow in the limb and relieve the ischemic stress therein, and
 c. repeating steps (a) and (b).

Yet in further embodiments, the method of performing remote ischemic conditioning may include alternating periods of complete occlusion and partial occlusion of the limb during the cuff inflation period. The use of alternating complete and incomplete occlusions may be done for various useful purposes, for example for detection of the current level of systolic blood pressure of the subject.

Although remote ischemic conditioning may be performed by using a manually-inflated cuff, for practical purposes the use of an automatic device is preferred. Such device 100 is generally shown in FIG. 1 and may include a controller 150 attached to or otherwise operably connected to the cuff 110. Various examples of such controllers and cuffs suitable for delivering of remote ischemic conditioning treatment have been described in greater detail in my previous patent applications. The present invention describes a number of methods and algorithms of operating such controllers to achieve a more gentle application of remote conditioning treatment.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 9 is a general chart of blood flow vs time showing another method of operating the cuff during the period of cuff deflation; and FIG. 10 shows a chart of venous pressure and various bladder pressures while measuring limb flow by temporarily occluding the venous return from the limb.

DETAILED DESCRIPTION OF THE PRESENT INVENTION

Figure 1:
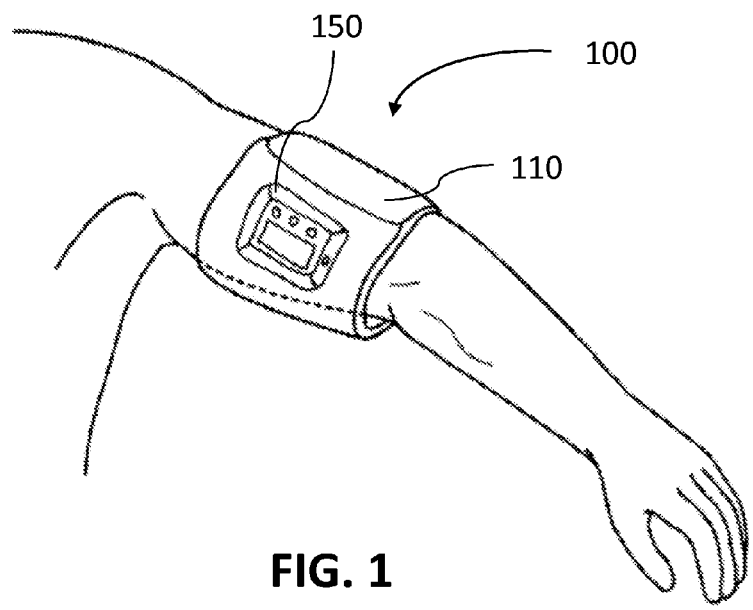
FIG. 1 is a general illustration of the device of the present invention.

FIG. 1 shows a general illustration of the device 100 including a cuff 110 and a controller 150, which may be attached to (removably or permanently) or otherwise operably connected to the cuff 110. The controller may have an internal microprocessor which may be programmed or otherwise configured to inflate the cuff according to a predetermined protocol of delivery of remote ischemic conditioning treatment.

During operation of the controller, the cuff may be inflated or deflated to certain levels of cuff pressure corresponding with certain levels of limb occlusion. The present description includes at least the following distinct states of cuff inflation and corresponding cuff pressures, listed here in the general order from low pressure to high pressure:

a. Full cuff deflation—no restriction in limb blood flow under the cuff, cuff pressure is at atmospheric level or below;

b. Retain-on-limb cuff state—low level of cuff inflation is applied, only enough to retain the cuff on the limb, cuff pressure is above atmospheric and well below diastolic blood pressure of the subject, generally between about 5 mmHg and about 20 mmHg;

c. Venous compression state—cuff is inflated to pressures ranging from about the venous pressure and up to about a diastolic pressure of the subject, generally from about 5 mmHg to about 80 mmHg—which causes initial venous compression, temporary occlusion and swelling of the limb veins caused by unrestricted inflow of arterial blood. Once venous pressure distal to the cuff equalizes in with the arterial pressure, blood continues to flow in and out of the limb under the cuff;

d. Initial limb occlusion state—cuff is inflated to a pressure sufficient to cause at least some degree of arterial compression and ischemic stress. In this state, the cuff may be inflated to a cuff pressure at least exceeding diastolic pressure of the subject—in order to initiate compression of the limb artery;

e. Partial limb occlusion state—cuff is inflated to or above a pressure corresponding in general to a mean arterial pressure, which is about half way between diastolic and systolic pressure of the subject, the artery of the limb is compressed by about a half and the blood flow is reduced from the level of blood flow when the artery was not compressed;

f. Ischemic stress state—the main limb artery is compressed by the cuff to a point of blood flow not yet stopped entirely but already reduced to a level causing at least a minimally effective ischemic stress for the purpose of remote ischemic conditioning treatment;

g. Complete limb occlusion state—cuff is inflated to a pressure known as Limb Occlusion Pressure, a minimum cuff pressure causing complete cessation of blood flow in the limb;

h. Systolic pressure or above—cuff is inflated to or above the systolic pressure of the subject. In many cases, depending on the width of the cuff, this pressure is above the limb occlusion pressure and the limb is unnecessarily over-compressed without inducing any more ischemic stress for the purposes of remote ischemic conditioning.

The cuff of the device may be inflated to and maintained at levels (a), (b), and/or (c) during the periods of cuff deflation and levels (d), (e), (f), (g), and/or (h) during the periods of cuff inflation.

Ischemic Stress

Normal tissue perfusion and tissue oxygenation can be described as a result of unrestricted blood flow supplying a certain mass of limb tissue with oxygen over time. Reduction of blood flow results in at least partial deprivation of limb tissue of oxygen and other nutrients. According to the present invention, to trigger a sufficiently strong remote ischemic conditioning effect to be useful for treatment purposes, limb tissue may be at least partially deprived of oxygen over each period of cuff inflation.

Figure 2:
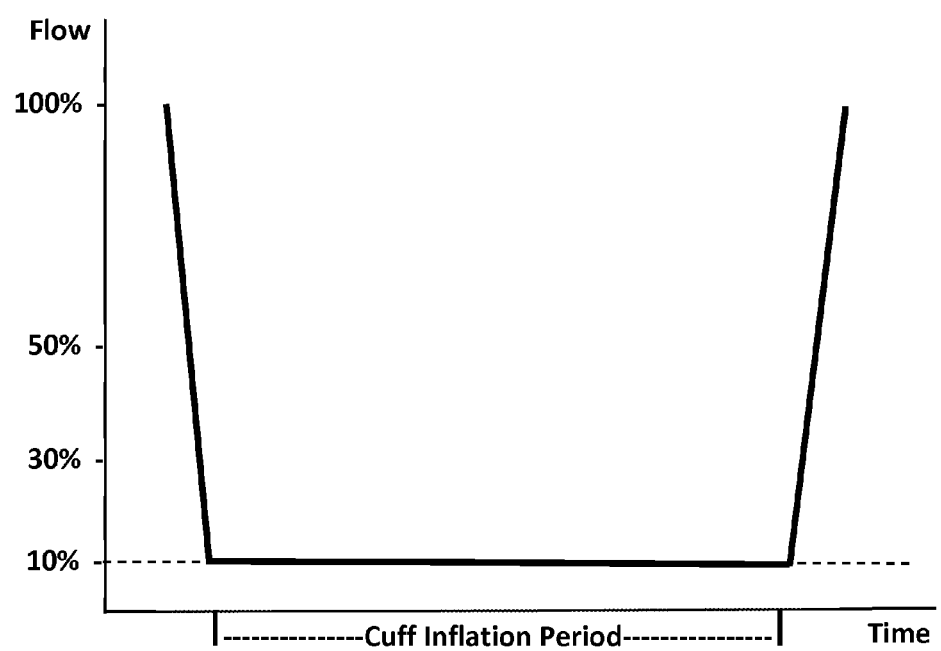
FIG. 2 is a general chart of blood flow vs time showing one method of operating the cuff during the period of cuff inflation.

Considering each treatment cycle and cuff inflation period individually, the total ischemic stress of limb tissue is a result of both the extent of reduction of blood flow and the duration of cuff inflation period. In embodiments, an ischemic stress threshold may be defined by a simple minimally effective predetermined threshold of blood flow reduction sufficient to generate the effect of remote ischemic conditioning. FIG. 2 shows an exemplary plot of blood flow (expressed as a percent of normal unrestricted blood flow in the limb) versus time. As seen in FIG. 2, blood flow reduction to about 10% or less of the unrestricted blood flow over the entire period of cuff inflation in each cycle of the treatment may be sufficient to generate remote ischemic conditioning benefit.

Importantly, the predetermined threshold of minimally effective blood flow reduction may be reached or exceeded in each cycle of the treatment—in other words, FIG. 2 shows the upper level of permitted blood flow in the limb. In embodiments, the blood flow may be at or below the predetermined threshold of allowed blood flow. Reducing blood flow below the predetermined threshold—all the way down to complete occlusion—may be done for a variety of useful purposes. One useful purpose for further reduction of blood flow may be to detect oscillometric oscillation amplitudes at various degrees of limb occlusion in order to detect current blood pressure of the subject with greater accuracy.

In embodiments, blood flow in the limb may be kept at a predetermined threshold of blood flow reduction for the entire period of cuff inflation. In other embodiments, blood flow may be reduced further down to achieve complete occlusion. In further embodiments, blood flow may be intermittently or continuously fluctuated at and below the predetermined threshold of blood flow reduction to vary the extent of ischemic stress, for example all the way down to complete occlusion. This may be accomplished by varying the cuff pressure so as to vary the extent of limb compression.

The predetermined threshold of minimally effective blood flow reduction may be defined in absolute or relative terms. In embodiments, the predetermined threshold of blood flow reduction may be defined as a certain portion or percentage of the unrestricted flow in the limb. Although FIG. 2 shows that level to be about 10% of the unrestricted flow, the present invention is not limited in this regard. In embodiments, the minimally effective threshold of blood flow reduction may be selected anywhere at or below about 40% of unrestricted blood flow, such as 40%, 35%, 30%, 25%, 20%, 15%, 10%, 5%, 2%, 1%, 0.1%, or any partial blood flow percentage inbetween.

Another method of defining a predetermined blood flow reduction threshold is to use absolute units of blood flow or alternatively units of blood flow normalized (divided by) limb tissue weight. Depending on the selecting the target limb to be an upper arm or a leg, the absolute blood flow threshold selection may be different. In an average person at rest, about 20% of the total cardiac output or about 1,000 ml/min is consumed by muscles, predominantly in arms and legs. For an average arm, the unrestricted blood flow at rest may be about 150 ml/min. In that case, the threshold of blood flow reduction may be defined as about 40% of that level or 60 ml/min or less, such as 60, 55, 50, 45, 40, 35, 30, 25, 20, 15, 10, 5, 1, 0.1 ml/min or any other value inbetween. For an average leg, the total blood flow at rest may be about 300 ml/min and so the threshold of blood flow reduction may be defined as below about 40% of that value or about 120 ml/min. In embodiments, the threshold of blood flow reduction in a leg may be defined as 120, 110, 100, 90, 80, 70, 60, 50, 40, 30, 20, 10, 5, 1, 0.1 ml/min or any other value inbetween as the invention is not limited in this regard. Adjustments to these numbers may be made to account for the size and weight of the subject.

Using tissue oxygenation parameters as the threshold of blood flow reduction, the average unrestricted tissue perfusion for an average 70 kg adult with a cardiac output of 5 l/min may be about 70 ml/min per 1,000 grams of tissue. Blood flow reduction threshold may be defined as 40% or less of that perfusion level, such as 28, 25, 20, 15, 10, 5, 4, 3, 2, 1, 0.1 ml/min of blood flow per 1,000 grams of limb tissue weight.

In further embodiments, the method of remote ischemic conditioning treatment may include avoiding complete occlusion of blood flow in the limb for longer than about 30 seconds or 1 minute at a time during the period of cuff inflation so as to reduce the risk of clot formation in the limb vessels. As the total period of cuff inflation may be longer than 1 minute, the methods of the present invention include operating the cuff in a manner to cause the blood flow to be below the predetermined threshold of blood flow reduction and at the same time avoid complete occlusion lasting about one minute or longer.

In further embodiments, the ischemic stress threshold needed for the purposes of remote ischemic conditioning may be defined as reducing blood flow to reach or stay below a cumulative limb oxygenation reduction threshold, defined as a product of a variable blood flow over the time of cuff inflation. More specifically, the extent of ischemic stress may be defined as an integral of blood flow or tissue oxygenation over time, or more specifically as an area under the curve of a chart plotting a limb blood flow (or limb tissue oxygenation) vs time. For constant blood flow at a level of a minimally effective blood flow reduction shown in FIG. 2 for example, that plot is a straight horizontal line and the area under the curve is a simple multiple of percent of blood flow by the time of cuff inflation.

The blood flow through the limb may be expressed in absolute terms, such as the actual flow of blood in cubic centimeters or milliliters of blood per one minute of time. The flow may also be normalized for tissue weight or volume, in which case the chart may be plotted to show the extent of tissue oxygenation expressed as cubic centimeters or ml of blood per minute of time per gram of limb tissue weight. The flow may also be expressed in relative terms such as percent of normal unrestricted flow as described above.

The time of blood flow reduction may be expressed in absolute terms such as minutes of cuff inflation time. It may also be expressed in relative terms such as percent of completion of a predetermined cuff inflation period.

The methods of performing a remote conditioning treatment of the present invention define reducing the flow of blood in the limb as being sufficient to at least achieve the minimum effective ischemic stress, which in turn may be defined as the area under the curve of flow versus time plot to be below a predefined cumulative limb oxygenation threshold. The cumulative limb oxygenation reduction threshold may be expressed as a percentage of full oxygenation with unrestricted blood flow, in which case it may be selected to be anywhere below about 40% of full unrestricted perfusion. In further embodiments, the predetermined cumulative limb oxygenation reduction threshold may be 40%, 35%, 30%, 25%, 20%, 15%, 10%, 5%, 0.1%, or any other percentage of full tissue perfusion inbetween. Using a threshold of limb oxygenation reduction rather than a threshold of blood flow reduction may be advantageous when dealing with reduced but variable blood flow during the cuff inflation period.

Figure 3:
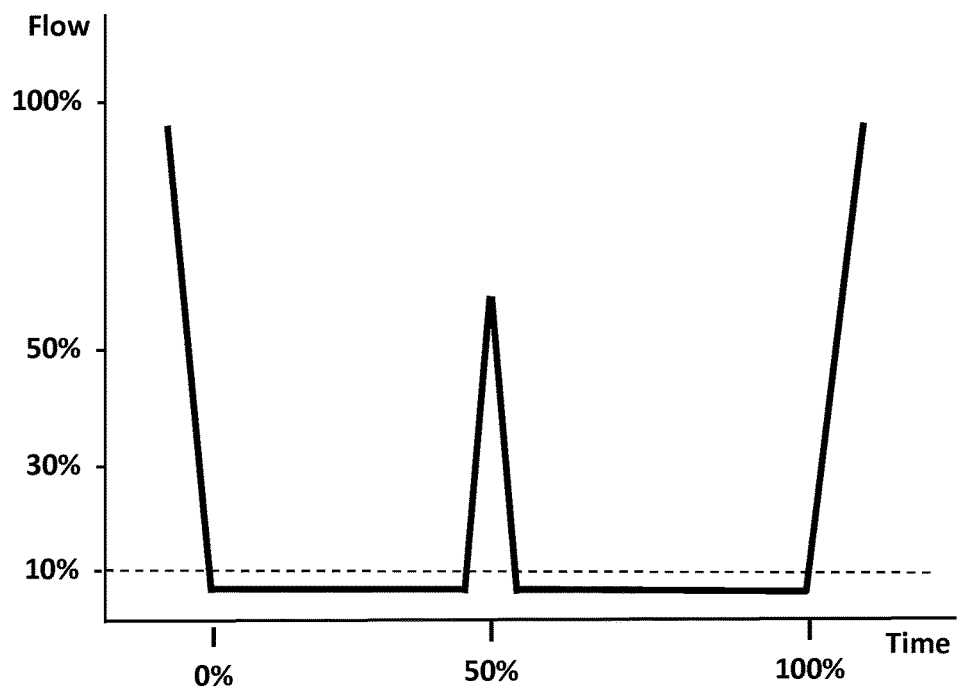
FIG. 3 is a general chart of blood flow vs time showing another method of operating the cuff during the period of cuff inflation.

FIG. 3 shows one example of variable blood flow in which the total area under the curve of flow vs time is below 10% of full oxygenation. In this example, the blood flow is expressed as a percentage of unrestricted blood flow (full flow is 100%) and the total duration of blood flow reduction is also expressed as a percentage of full cuff inflation period (entire cuff inflation period is 100%). In this example, while during most of the cuff inflation period the blood flow is reduced to about 7% of normal unrestricted value, about half the way into the cuff inflation, blood flow is allowed to increase for a short period of time. Despite a spike of blood flow in the middle of the cuff inflation period, the total area under the curve of blood flow during the entire cuff inflation period is still under about 10% of full tissue perfusion (dashed line in FIG. 3), which in this example satisfies the requirement for reaching a sufficiently strong ischemic stress to cause remote ischemic conditioning benefits.

One or several short-term increases of blood flow to levels at or above 20%, 30%, 50% of its unrestricted level or even to full unrestricted flow may not be detrimental for the purpose of causing sufficient cumulative ischemic stress, while at the same time these occasional increases in blood flow may be useful to detect blood pressure of the subject with greater accuracy, reduce the risk of clot formation or for other beneficial purposes. In embodiments, temporary increases of blood flow above the predetermined threshold may last only a few seconds so as not to diminish the overall cumulative extent of ischemic stress. Such durations of increased blood flow may last 1, 2, 3, 5, 10, 15, 20 seconds or any duration inbetween as the invention is not limited in this regard. Such increases in blood flow may also be expressed in the number of heart beats such as 1, 2, 3, 5, 10, 15, 20, 25, 30 heartbeats or any number of heartbeats inbetween during which the blood flow in the limb tissue is increased.

Figure 4:
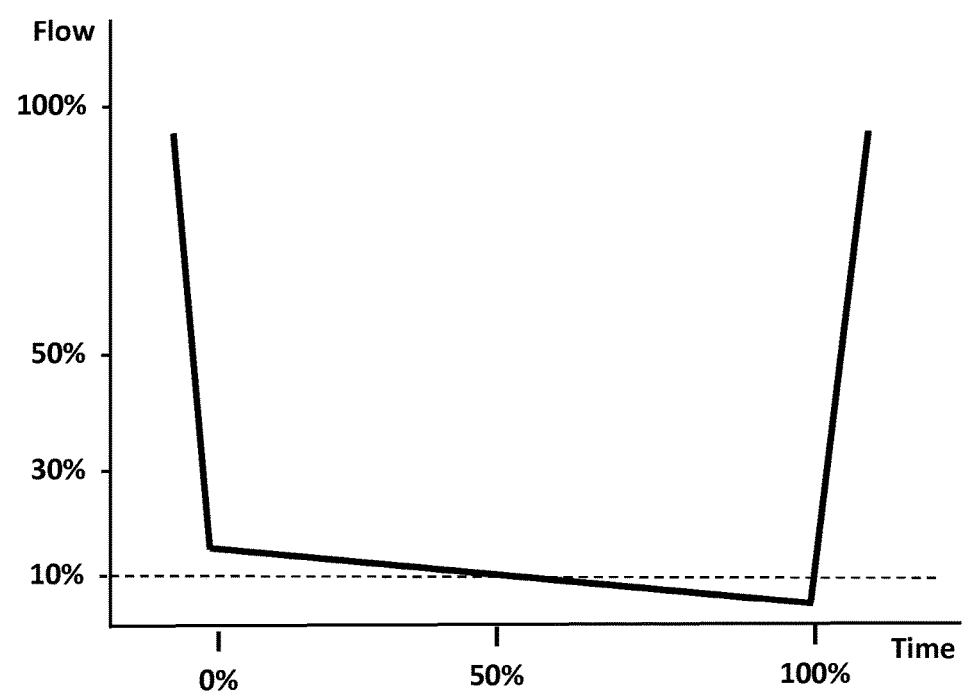
FIG. 4 is a general chart of blood flow vs time showing a further method of operating the cuff during the period of cuff inflation.

FIG. 4 shows another example of variable degree of blood flow reduction during the period of cuff inflation to cause ischemic stress. In this case, blood flow reduction is gradually extended from initial less restrictive level to the final more restrictive level. Of note is that the area under the curve in FIG. 4 which defines total limb tissue oxygenation is about the same as in FIG. 2 and FIG. 3. Gradual increase in limb compression may be deployed to improve subject's comfort at the beginning of ischemic duration interval.

Figure 5:
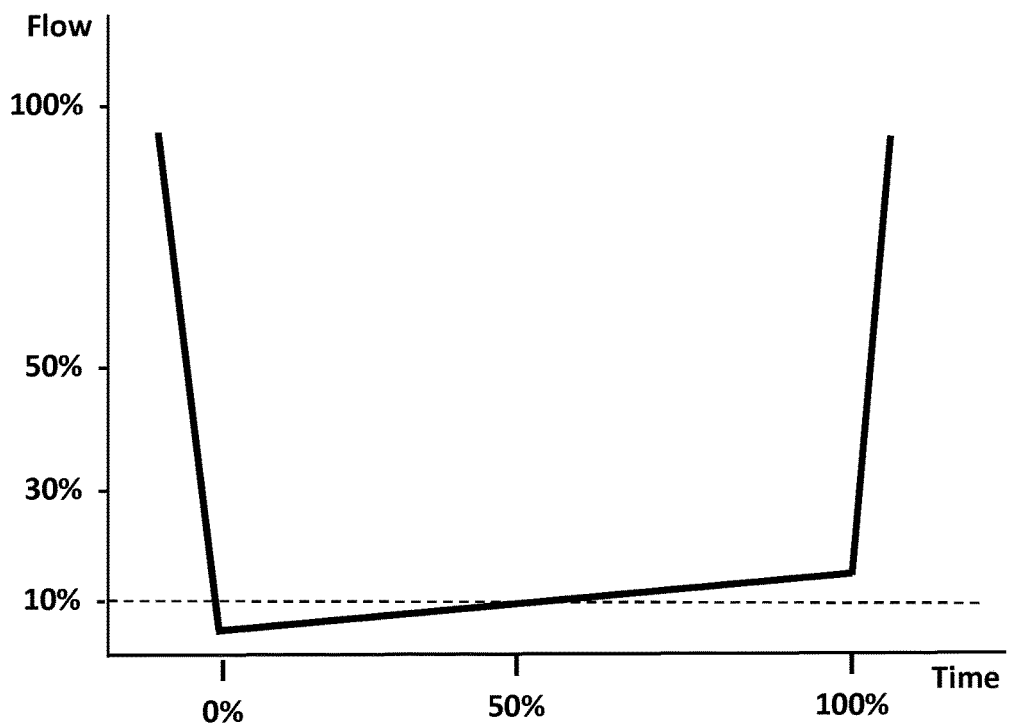
FIG. 5 is a general chart of blood flow vs time showing a further yet method of operating the cuff during the period of cuff inflation.

FIG. 5 shows another example of operating the cuff—this one is designed to gradually decrease limb compression during the period of cuff inflation. This strategy may be used to reduce subject discomfort towards the end of the cuff inflation period when the limb feels most cold and numb. Note that the general extent of oxygen deprivation of the limb tissue is still about the same as in the previous figures as evident by the area under the curve during the cuff inflation period.

Figure 6:
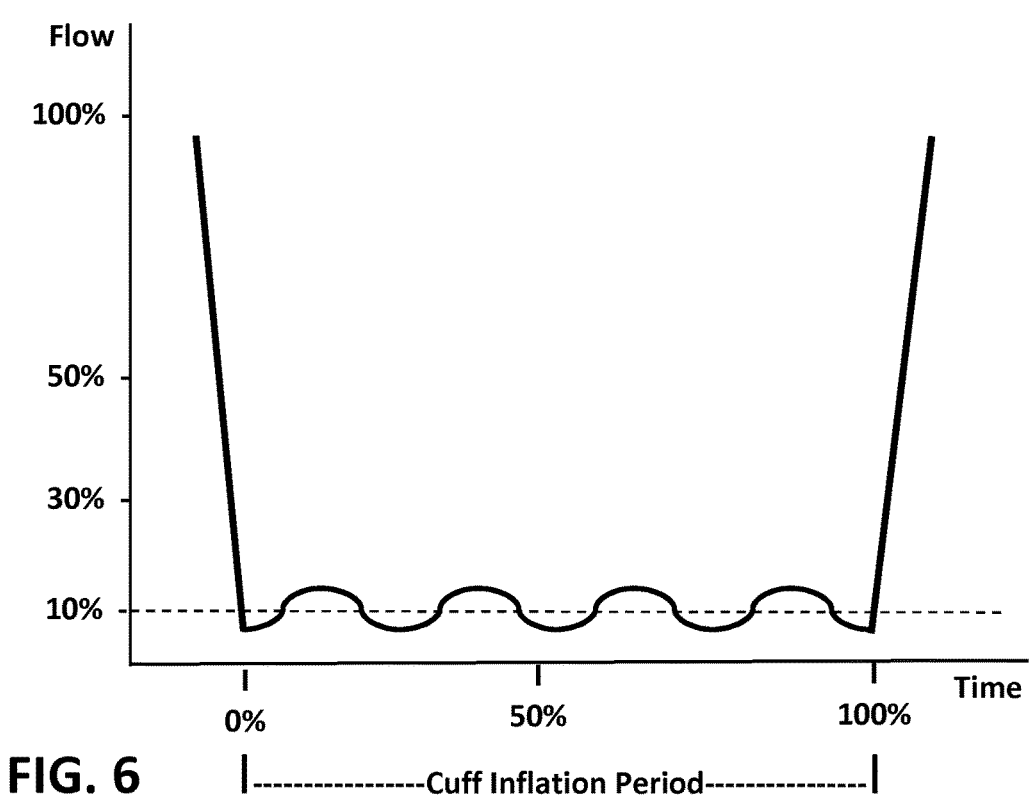
FIG. 6 is a general chart of blood flow vs time showing yet another method of operating the cuff during the period of cuff inflation.

FIG. 6 shows yet another example of operating the cuff to cause about the same degree of ischemic stress as in the previous figures—in this case the cuff pressure is varied on a predetermined schedule to cause periodic increase and decrease in limb compression and subsequently fluctuating levels of blood flow reduction and variable tissue oxygenation. Periodic partial relief of ischemia may be used to reduce discomfort of a subject during the treatment. This may be achieved by periodic varying of cuff pressure to change the extent of limb compression.

Figure 7:
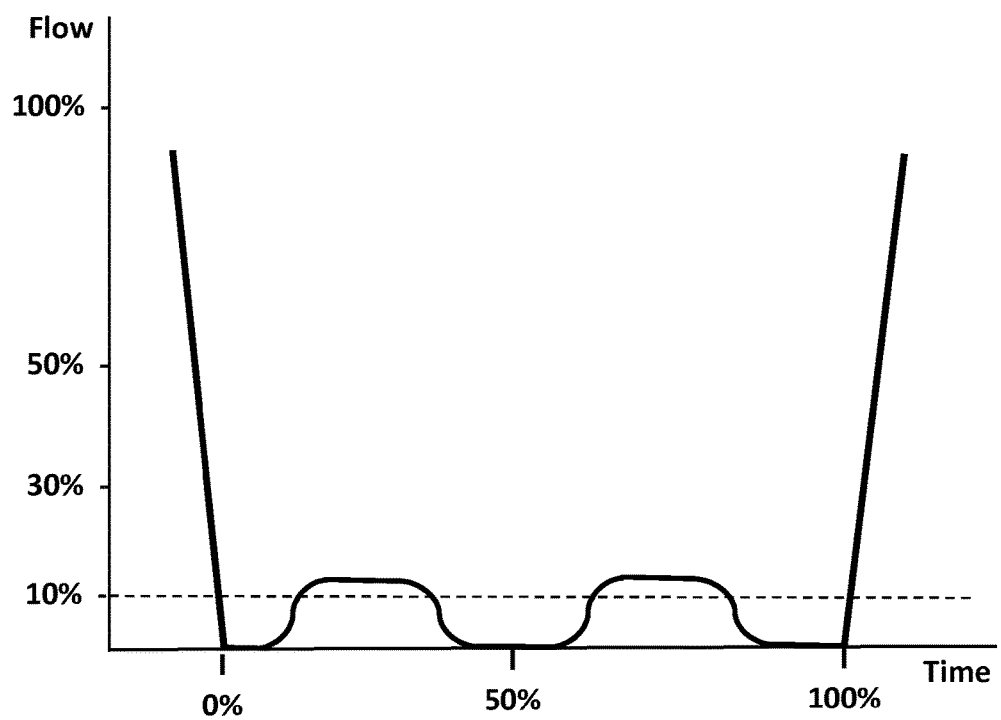
FIG. 7 is a general chart of blood flow vs time showing yet another method of operating the cuff during the period of cuff inflation.

While all previous examples show a deep reduction but not complete occlusion of blood flow in the limb, the present invention also contemplates having at least one or several limited periods of complete occlusion and total blood flow cessation in the limb during the period of cuff inflation in at least one cycle of the remote ischemic conditioning treatment. FIG. 7 shows one example of such technique in which the cuff is initially inflated to cause full occlusion and then twice during the period of cuff inflation such full occlusion is partially relieved allowing for at least a small amount of blood to go pass the cuff. In embodiments, each period of full occlusion may not exceed about one minute so as to reduce the risk of thrombus formation in the limb. More than one fluctuation of cuff pressure may be used throughout the period of cuff inflation depending on its total duration.

Operating the cuff in various modes shown in FIGS. 2-7 may need to be adjusted if blood pressure of the subject changes—this may be accomplished for example by monitoring the amplitude of oscillations of the cuff pressure or by using other blood pressure or flow monitoring techniques as described throughout this document.

Monitoring the initial and ongoing degree of blood flow reduction as well as detecting onset of complete limb occlusion may be done utilizing various manual or automated techniques. In embodiments, some examples of the available techniques to assess the blood flow level in the limb may include manual or machine-implemented detecting of Korotkoff sounds, evaluation of oscillometric amplitudes, direct or indirect blood flow monitoring past the cuff, measuring tissue temperature or heat dissipation ability, measuring limb tissue oxygenation levels, SPO2, and monitoring a plethysmograph signal.

Estimating the extent of blood flow occlusion may also be done using the cuff pressure—alone or in combination with other techniques mentioned above. In embodiments, full or partial oscillometric envelope information may be collected at the beginning or the end of at least one treatment cycle. This information may also be collected at least once or on a scheduled basis during the period of cuff inflation. The term "oscillometric envelope" is used herein to describe a curve over the peaks of oscillometric oscillation amplitudes obtained at various cuff pressures—such as for example covering the range of diastolic to systolic blood pressure of the subject. In a typical oscillometric envelope, a maximum peak amplitude may be determined and used to detect the corresponding mean arterial pressure (MAP). Systolic and diastolic pressures of the subject may be then calculated using known ratios and equations. Alternatively, systolic and/or diastolic blood pressure may also be determined using a first derivative of the oscillometric envelope curve or other signal processing techniques.

Significant reduction in limb blood flow may be caused by a cuff pressure being at or above a mean arterial pressure, which corresponds to the maximum amplitude of oscillometric oscillations—at a point of arterial occlusion when the artery is approximately compressed by about 50%. This degree of compression leads to maximum transmission of arterial pressure fluctuations from the artery to the cuff compressing the limb and hence causes the cuff pressure oscillations to exhibit maximum amplitude. Reduction in arterial cross-section by about 50% at this point may not necessarily correspond to a 50% reduction in blood flow but this reduction may be minimally effective to cause an ischemic stress of sufficient extent to cause remote ischemic conditioning effects. The advantage of using MAP as a marker of the minimum effective stress is that it can be easily determined using only the cuff pressure signal and no other additional sensors.

In embodiments, the ischemic stress threshold for the target of inflating the cuff may also be determined as MAP plus a predetermined MAP offset, which may be expressed in absolute units such as mmHg or as a percentage of the detected MAP value. According to the invention, the minimum effective cuff pressure to cause sufficient ischemic stress may be achieved at a detected MAP pressure plus a predetermined MAP offset of up to 60 mmHg such as for example 1, 5, 10, 15, 20, 25, 30, 35, 40, 45, 50, 55, or 60 mmHg or any number of mmHg inbetween. In other embodiments, the predetermined MAP offset may be up to 50% of detected MAP such as 1, 2, 3, 4, 5, 6, 7, 8, 9, 10, 15, 20, 25, 30, 35, 40, 45, 50 percent thereof or any other predetermined value inbetween as the invention is not limited in this regard.

In further embodiments, a current level of detected systolic blood pressure may be used to define the minimally effective cuff inflation target pressure. Depending on the width of the cuff, blood flow may or may not be fully occluded when the cuff is inflated to systolic blood pressure of the subject. In embodiments, the minimally effective cuff pressure may be selected to be within a range of pressures determined using a systolic blood pressure of the subject. Such range may extent from a lower value calculated as detected systolic pressure minus a predetermined first systolic pressure offset and end at a higher value calculated as detected systolic pressure plus a predetermined second systolic pressure offset. In embodiments, the first systolic pressure offset and the second systolic pressure offset may be defined in absolute units such as mmHg, or as a percentage of detected systolic pressure. The first systolic pressure offset may be 1, 5, 10, 15, 20, 25, 30, 35, 40, 45, 50 mmHg or any number of mmHg inbetween. The first systolic pressure offset may also be defined as up to 50% of systole such as 1, 2, 3, 4, 5, 6, 7, 8, 9, 10, 15, 20, 25, 30, 35, 40, 45, 50 percent thereof or any other predetermined value inbetween as the invention is not limited in this regard. The second systolic pressure offset may be 1, 5, 10, 15, 20, 25, 30, 35, 40, 45, 50 mmHg or any number of mmHg inbetween. The second systolic pressure offset may also be defined as up to 20% of detected systolic blood pressure of the subject such as 1, 2, 3, 4, 5, 6, 7, 8, 9, 10, 15, 20 percent thereof or any other predetermined value inbetween as the invention is not limited in this regard.

Once the cuff is inflated to a target pressure to cause a predetermined level of limb compression and blood flow reduction, it may be maintained at this level of limb compression during a part of or throughout the entire period of cuff inflation. Blood pressure of the subject may change over time so continuous or intermittent adjustments to cuff pressure may be needed to maintain the desired level of limb compression. One way to achieve this is to determine the amplitude of oscillometric oscillations once the desired initial limb compression is achieved and then adjust the cuff pressure to maintain that level of oscillometric amplitude for the desired portion of the cuff inflation period. If blood pressure of the subject increases during ischemic duration interval, the amplitude of cuff pressure oscillations would increase as well—in that case the cuff pressure may be increased until the amplitude of oscillations is reduced back to the desired initial level. If on the other hand, the blood pressure of the subject goes down while the cuff is inflated, the amplitude of oscillations in the cuff would diminish as well—in that case, the cuff may be gradually deflated until the amplitude has reached the same initial level. Periodic or continuous dithering of cuff pressure may be needed to assure maintaining the desired level of limb compression regardless of fluctuating blood pressure of the subject.

Reperfusion

Similarly to the above described concept teaching that complete occlusion may not be necessary during the entire period of cuff inflation, the present invention describes methods of increasing blood flow during cuff deflation period that may or may not reach full deflation of the cuff and complete restoration of blood flow in the limb.

According to the present invention, after a period of cuff inflation a significant enough increase in blood flow in the limb is needed for the purposes of remote ischemic conditioning treatment. The increase in blood flow needs to be sufficient to at least relieve the ischemic stress developed during the preceding period of cuff inflation. While complete deflation of the cuff to remove all compression of the limb is effective in restoring full perfusion, it may not be the only way to trigger remote ischemic conditioning benefits while achieving other useful purposes.

As described above, tissue oxygenation is a result of blood flow as a function of time. Using that notion, tissue oxygenation may be expressed as the area under the curve as described above plotting blood flow or tissue oxygenation as a function of time. Restoring tissue perfusion to an unrestricted level throughout the entire reperfusion duration of cuff deflation period may be viewed as 100% reperfusion and complete tissue oxygenation. According to the present invention, partial reperfusion caused by increased but not fully restored blood flow may also be sufficient to deliver clinically effective remote ischemic conditioning treatment.

In embodiments, during a period of cuff deflation, blood flow may be increased to a level at or above a predetermined reperfusion threshold. The reperfusion threshold may be defined in absolute or relative terms using for example a measure of blood flow in percentage points or ml/min. Depending on the choice of a limb and the weight of the subject, the reperfusion threshold may be selected to be at least 40% of unrestricted blood flow level so as to relieve ischemic stress. In embodiments, the reperfusion threshold may be selected to be 40, 50, 60, 70, 80, 90, 99, 100, 105, 110 percent of unrestricted blood flow or any other level inbetween. Notably, unrestricted flow following ischemic duration of cuff inflation period may temporarily exceed the previous levels of blood flow by up to 10% due to flow-mediated dilatation effect.

Using absolute values of blood flow as a measure for reperfusion threshold, for an arm the reperfusion threshold may be selected to be 60 ml/min of blood flow or higher, such as 60, 65, 70, 75, 80, 85, 90, 100, 110, 120, 130 ml/min or any other value above 60 ml/min as the present invention is not limited in this regard. For a leg, the reperfusion threshold may be selected to be at or above 120 ml/min of blood flow, such as 120, 130, 140, 150, 160, 170, 180, 190, 200, 220, 240, 260, 280, 300, 320, 340, 360 ml/min or any other level of blood flow inbetween.

The predetermined reperfusion threshold value may also be selected by normalizing blood flow to the tissue weight. Assuming a normal average blood flow of 5 l/min in a 70 kg adult subject, the average unrestricted blood flow per unit weight of tissue is about 70 ml/min per 1,000 grams of tissue weight. In embodiments, the cuff may be deflated to reach or exceed at least about 40% of that value or about 28 ml/min per 1,000 grams of limb tissue weight. In other embodiments, the threshold may be established at 30, 35, 40, 45, 50, 55, 60, 65, 70 or more ml/min per 1,000 grams of limb weight.

Figure 8:
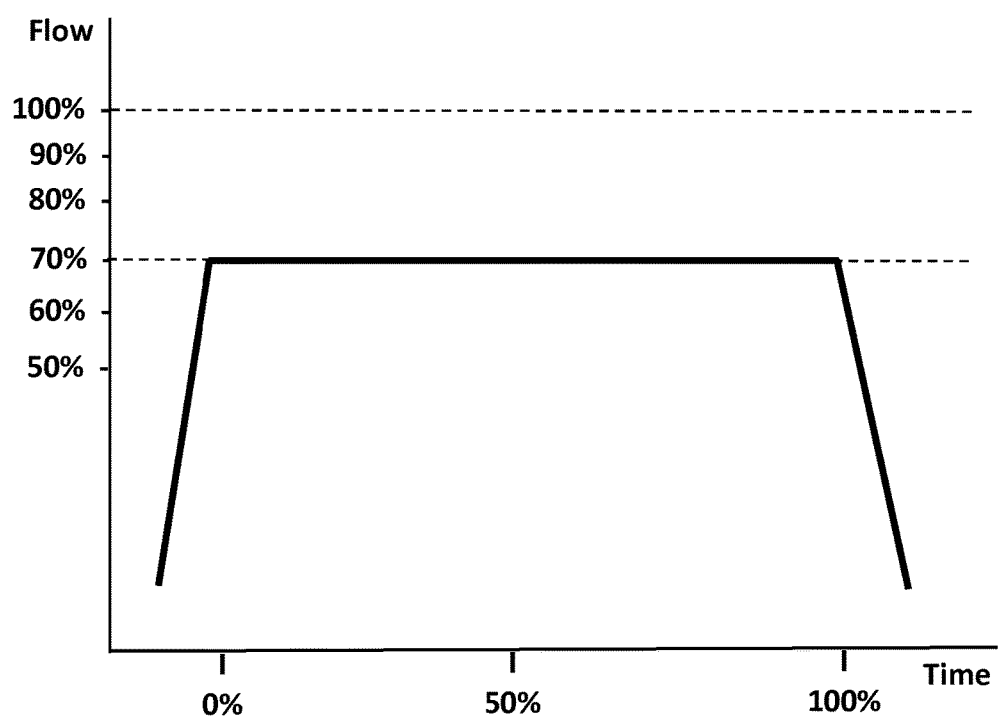
FIG. 8 is a general chart of blood flow vs time showing one method of operating the cuff during the period of cuff deflation.

FIG. 8 shows a simple example of operating the cuff during the cuff deflation period in which ischemic stress is relieved by increasing the blood flow to a predetermined reperfusion threshold of about 70% of the previously unrestricted blood flow level.

In addition to increasing blood flow to a predetermined constant reperfusion threshold as seen in FIG. 8, the present invention contemplates providing variable flow during cuff deflation period. Such flow of blood in the limb while variable has to satisfy the requirement of providing minimally effective tissue oxygenation so as to cumulatively relieve ischemic stress and support proving remote conditioning treatment to the subject. FIG. 9 shows one example of variable blood flow during cuff deflation period in which about half way into the duration of cuff deflation, the cuff is inflated to reduce blood flow in the limb for a short period of time. One or several such flow reductions lasting few seconds or few heartbeats may be instrumental to record the current oscillometric envelope and detect the current level of subject's blood pressure, at least a diastolic blood pressure value and perhaps the mean arterial blood pressure as well. In other embodiments, full occlusion of blood flow may be performed during the period of cuff deflation so as to characterize the entire blood pressure of the subject including systolic, mean arterial and diastolic blood pressure thereof.

In embodiments, the reperfusion threshold may be defined as about 70% of unrestricted perfusion in the limb. In other embodiments, the reperfusion threshold may be defined as at least 50% or greater restoration of limb tissue oxygenation, such as 50, 60, 70, 80, 90, 99 percent of tissue oxygenation or any value inbetween.

Reperfusion threshold may also be defined by cuff pressure—in absolute terms or in relation to blood pressure of the subject. In embodiments, the reperfusion threshold may be defined as deflating the cuff to about 120 mmHg or less, such as 120, 110, 100, 90, 80, 70, 60, 50, 40, 30, 20, 10, 5, 1 mmHg or any other level of pressure inbetween.

Associating the target cuff pressure with blood pressure of the subject during the period of cuff deflation may also be used. In some embodiments, the target cuff pressure during the cuff deflation period may be selected to be below limb occlusion pressure. In other embodiments, the target cuff pressure may be selected to be below systolic blood pressure. Yet in further embodiments, the target cuff pressure may be selected to be about or below mean arterial pressure of the subject. In further embodiments, the target cuff pressure may be selected to be about or below the diastolic blood pressure of the subject.

The respective thresholds for ischemic stress and reperfusion discussed above have been generally discussed with reference to an average subject having approximately normal blood circulation and tissue oxygenation. Adjustments to these thresholds may be made depending on a number of factors and circumstances for each individual subject. Examples of such factors that may necessitate adjustments for operating the cuff include:

a. Abnormally high or low baseline tissue oxygenation, which may result from recent exercise or another physical activity, breathing at high altitude, breathing oxygen-rich or oxygen-poor gas mixture (such as through a ventilator), breathing near a fire where oxygen is consumed by flames, breathing in smoke
   b. Inability of lungs to oxygenate blood
   c. Inability of tissue to use oxygen such as occurs for example in cyanide poisoning
   d. Decrease in oxygen content in blood, such as occurs in anemia or chronic hypoxemia
   e. Recent blood transfusion
   f. Severe recent blood loss due to trauma, accident or another cause
   g. Cold or hot ambient conditions
   h. Abnormally high or low body temperature causing respectively an increased or decreased oxygen demand
   i. Abnormal hemoglobin content in blood
   j. Abnormal oxygen saturation
   k. Reduced cardiac output
   l. Hypertension or hypotension
   m. Vasoconstriction or spasm of limb vessels, such as caused by certain medications or electric shock
   n. Acid-based imbalance such as acidosis or alkalosis
   o. Arterial gases imbalance In these cases, the methods of the invention may be adjusted to achieve remote conditioning effect by periodically inflating the cuff to reduce blood flow and reduce tissue oxygenation below an adjusted ischemic stress threshold for a predetermined time of at least one minute—and alternating with periods of cuff deflation when blood flow is increased to a level at or above the adjusted reperfusion threshold so as to relieve the ischemic stress.

In further embodiments of the methods of the present invention, identifying a subject with abnormally low or abnormally high level of tissue oxygenation prior to initiation of remote ischemic conditioning treatment may necessitate taking additional steps aimed at restoring the limb tissue oxygenation to be as close to normal as practical. Such additional steps may be taken prior to, during or shortly after the administration of the remote ischemic conditioning treatment. One example of such additional treatment may be fluid infusion or blood transfusion that may take place for a victim of severe blood loss in order to relieve possible low cardiac output and/or hypotension. Another example is moving a subject away from fire or smoke and possibly initiating oxygen-rich breathing to restore normal tissue oxygenation for a burn victim suffering from prior smoke inhalation.

Automatic Single-Bladder Devices for Remote Ischemic Conditioning Via Partial Limb Occlusion Some or all of the above described methods of inflating and deflating a cuff for the purposes of providing a subject with remote ischemic conditioning treatment may be implemented in an automatic controller operably connected to the cuff. The controller may be equipped with a microprocessor that may be programmed or otherwise configured to execute the methods of the invention upon its activation. The microprocessor may contain an imbedded computer memory containing software designed to implement the methods of the invention. Alternatively, the software may reside on a removable piece of hardware such as a memory stick, which may be plugged into the controller prior to its activation. In further embodiments, the software may reside on a central server and the controller may be operably connected to the server for at least a portion of time prior to or during the treatment. Such server connection may be accomplished using known wired or wireless connection means and protocols. One advantage of using a central server to control inflation and deflation of the cuff via a local controller is the ability to retain the record of the procedure as well as record blood pressure of the subject with the ability to integrate into the hospital system of data recording. Another advantage is the ability to provide the most up to date algorithm from a single central server to all local controllers—without the need to update each controller individually. The controller at the side of the subject may also be equipped with wired or wireless transmission capability to record all pertinent data and transmit this data to a central data recording facility.

In some embodiments, the cuff may be configured for the purposes of remote ischemic conditioning with a single inflatable bladder configured to be placed over the limb of a subject and capable of reducing or stopping blood flow in the limb upon inflation thereof. In that case, the controller may be equipped with pneumatic components (air pump, valves, reservoirs, etc.) configured to inflate and deflate this single bladder according to the methods of remote conditioning treatment described above. The controller may also be equipped with one or more sensors, such as a bladder pressure sensor so as to monitor the state of inflation or deflation of the cuff bladder. The device may further include one or more sensors to monitor other parameters characterizing the subject or the process of treatment delivery. Examples of such sensors include tissue oxygenation sensors, blood flow sensors, temperature sensors, microphones or other sensors to detect Korotkoff sounds, SPO2 sensors, etc.

The controller may be operably connected to the cuff, such as directly attached thereto or incorporated therewith. The controller may be configured upon activation to deliver remote ischemic conditioning treatment by performing a plurality of remote ischemic conditioning treatment cycles, each treatment cycle generally comprising a period of cuff inflation and a period of cuff deflation. During at least one period of cuff inflation, the controller may be operated to cause the cuff to be inflated to and maintained at or above a pressure sufficient to cause at least a partial reduction of blood flow in the limb in order to produce an ischemic stress therein lasting for at least about one minute. The controller may further be operated during at least one period of cuff deflation to cause the cuff to deflate at least to a degree sufficient to increase blood flow in the limb and relieve the ischemic stress. In further embodiments, the controller may be configured to avoid complete occlusion of the limb by the cuff lasting more than about one minute during at least one of remote ischemic conditioning treatment cycles. In further yet embodiments of the invention, the controller may be further configured to inflate the cuff during at least a portion of cuff inflation period to a pressure at or below a lesser of either the systolic blood pressure of the subject or the limb occlusion pressure of the subject so as to assure at least a partial flow of blood under the cuff. In further yet embodiments, the controller may be programmed to maintain the cuff pressure at or above the minimum effective cuff pressure selected to reduce blood flow in the limb by 90% or more from its original unrestricted level.

Desired cuff pressure and level of blood flow reduction during each period of cuff inflation may be maintained or varied depending on the desired level of ischemic stress and fluctuating blood pressure of the subject—for example by using the methods described above in greater detail. In embodiments, at least one or all periods of cuff inflation may include at least one period of complete blood flow occlusion and at least one period of partial blood flow occlusion. In further embodiments, one or more treatment cycles may include alternating periods of complete and partial blood flow occlusion.

In some embodiments, the controller may be programmed to inflate the cuff to a pressure above the systolic blood pressure of the subject or above the limb occlusion pressure of the subject, whichever is greater—to cause complete cessation of blood flow in the limb at the beginning or at any time during the cuff inflation period. The controller may be further programmed to deflate the cuff once or periodically (such as on a scheduled basis) to a pressure at or below the systolic blood pressure or the limb occlusion pressure of the subject, whichever is less depending on the width of the cuff and other factors, so as to allow a small amount of blood to pass under the cuff into the limb arteries. This procedure may be used to determine oscillometric oscillations in the cuff, which may be further used in determination of at least the updated systolic blood pressure of the subject. Signal processing operations and/or further deflation of the cuff may be used to detect mean arterial pressure, diastolic blood pressure, heart rate and other parameters of interest for the subject of the treatment. The entire process of collecting data for detecting the updated value for one or more parameters characterizing blood pressure of the subject may be done within a few seconds or a few heart beats of the subject. Once the data is collected, the cuff may be inflated to pressures at or above the updated limb occlusion pressure so as to restore complete cessation of blood flow in the limb until the next scheduled cuff deflation process. In alternate embodiments, cuff pressure may be continuously fluctuated or dithered to go above and below limb occlusion pressure so as to continuously or at least frequently detect the level of systolic blood pressure of the subject or other parameters of interest. It is estimated that occasional deflation of the cuff pressure to touch on systolic blood pressure of the subject may not cause more than a few percentage points of blood flow to pass under the cuff throughout the entire period of cuff inflation, whereby frequent determination of updated blood pressure of the subject may be done advantageously without jeopardizing the clinical benefit of remote ischemic conditioning treatment.

In further yet embodiments, the controller may be programmed to keep the cuff pressure generally above the point of reducing the blood flow by about 90% from its unrestricted levels. Care may be taken to assure that the cuff is not inflated to completely occlude limb blood flow for extended periods of time such as lasting one minute or longer—so as to reduce a risk of forming clots in the limb vasculature.

Upon expiration of a predetermined period of time for cuff inflation or another signal that sufficient ischemic stress has been achieved, the controller may be configured to initiate the period of cuff deflation. As compared with traditionally practiced full deflation of the cuff, the present invention discloses systems that may be configured to not fully deflate the cuff for the entire period of cuff deflation. As explained in greater detail above, the cuff may be deflated sufficiently to increase blood flow and relieve ischemic stress but at the same time the cuff may have some residual pressure therein which may be varied for useful purposes during the period of cuff deflation.

In some embodiments, the cuff pressure may be maintained at a low level of pressure to retain the cuff on the limb and avoid its slipping or changing location. That level of "retain on limb" cuff pressure may be about 5 mmHg or another suitably low level of pressure, for example 1, 2, 3, 4, 5, 10, 15 or about 20 mmHg.

In further embodiments, the cuff pressure may be increased for short periods of time so as to detect oscillometric oscillations once or on a periodic scheduled basis during the period of cuff deflation. Such periods of time may be as short as a few seconds and may be scheduled every 20, 30, 45, 60, 90, 120 seconds or any other interval during the period of cuff deflation. Cuff pressure may be increased to a predetermined fixed level or until sufficient oscillometric data is obtained as described above. Once the period of cuff deflation is finished, the controller may be programmed to initiate a subsequent period of cuff inflation. After all predetermined periods of cuff inflation and cuff deflation are complete, the controller may be programmed to fully deflate the cuff and optionally communicate to the user that the procedure is complete.

Automatic Dual-Bladder Devices for Remote Ischemic Conditioning Via Partial Limb Occlusion Additional advantageous functionality and/or physiologic monitoring may be performed when the cuff includes more than one inflatable bladder. Using multiple bladders may increase the overall width of the cuff, which in turn may allow delivery of the treatment at lower cuff pressures while still performing accurate detection of blood pressure of the subject during the treatment. In embodiments, the cuff may include two or more inflatable bladders, such as a distal bladder and a proximal bladder. Proximal bladder is the one that is closer to the heart and generally placed above the distal bladder on the limb. Both bladders may be placed on a limb next to each other, overlap with each other or be positioned with some space inbetween. At least one of the inflatable bladders, such as a distal one for example, may be made to have a width corresponding to a width of a standard blood pressure monitoring cuff so it can be used to detect the blood pressure of the subject. In other embodiments, when the width of the cuff does not match traditional cuff width recommendations, computational correction may be implemented to compensate for this mismatch. For example, measured blood pressure may be computationally increased to compensate for narrow width of the bladder or computationally decreased to compensate for wider bladder width. The total width of the cuff having multiple inflatable bladders may be as long as the entire upper arm and even span some area of the elbow or below the elbow.

The controller may be configured to operate each inflatable bladder independently by inflating and deflating each bladder separately. In other embodiments, the controller may be configured to connect both or all bladders together to equalize pressures therein from time to time if required. These configurations are described in greater detail in my previous patents cited above.

One advantageous method of operating two bladders is described below. Upon activation of the controller, the distal bladder with the width of a traditional blood pressure cuff may be inflated first from initial zero pressure to a first target pressure, such as 140, 150, 160, 170, 180, 190, 200, 210, 220 mmHg or any other suitable pressure at or above systolic pressure of the subject. Another way to determine a first target pressure is to measure the current systolic blood pressure of the subject and inflate the distal bladder to or above that measured pressure as described next. Oscillometric data may be collected on the way up during initial inflation of the distal bladder and the blood pressure of the subject may be determined therefrom. The distal bladder may be inflated continuously or in predetermined increments of cuff pressure. Once oscillometric data is recorded, the systolic blood pressure may be determined using known oscillometric techniques.

The proximal bladder may then be inflated—for example to the same first target pressure as the distal bladder. During inflation of the proximal bladder, amplitude data of oscillometric oscillations may also be recorded. Advantageously, already known MAP and systolic pressure of the subject may be correlated to oscillations amplitudes in the proximal cuff, so that data is recorded correlating amplitudes of oscillations in the proximal bladder to the pressure in the proximal bladder at previously measures MAP and systolic blood pressure of the subject. Both inflatable bladders may then be inflated to the first target pressure, such as for example to completely occlude the limb blood flow.

At some predetermined point of the cuff inflation period, the proximal inflatable bladder or both inflatable bladders together may be slowly deflated to record oscillometric oscillations therein. In embodiments, the proximal bladder may be deflated to detect the current systolic pressure, for example by measuring the amplitude of oscillometric oscillations therein and matching that to the previously detected amplitudes corresponding to the previously measured systolic blood pressure. Reaching the same amplitude of oscillations in the proximal bladder as with the previous systolic blood pressure may be used to detect the current updated value of the systolic blood pressure.

Other criteria for reaching sufficiently low pressure in the proximal or distal bladder may also be used to stop further deflation of the bladders, such as fitting a curve to the peaks of oscillometric oscillations and detecting systolic pressure from the first derivative of that curve. Once the updated blood pressure of the subject is determined, both bladders may be inflated at or above the newly detected systolic pressure or at or above the calculated updated limb occlusion pressure based on the current systolic pressure—so that blood flow may be either entirely occluded or partially reduced to cause ischemic stress as described above. The cuff pressure in one or both bladders may be dithered or fluctuated again from time to time so as to keep up with fluctuating blood pressure of the subject.

Upon completion of the scheduled cuff inflation period, the proximal bladder may be deflated first—so as to no longer restrict arterial blood flow. The distal bladder may be deflated thereafter—the process of its slow deflation may be used to record the full extent of the oscillometric envelope on the way down. That allows accurate detection of updated systolic, diastolic and MAP blood pressures of the subject, which then may be displayed to the user or the clinical professional. The controller may then be configured to execute the period of cuff inflation and relieve the ischemic stress for a specified duration of time.

Detection of Limb Blood Flow Using a Dual-Bladder Cuff

During one or more periods of cuff deflation it may be useful to determine the extent of blood flow in the cuff. Blood flow information may be instrumental to adjust the cuff pressure so as to cause sufficient level of reperfusion and relieve ischemic stress. Blood flow may also be useful to determine the extent of flow mediated dilatation—a phenomenon of compensatory increase in blood flow in the limb following a period of ischemia. The extent of this temporary increase in limb blood flow may be indicative of the endothelial health or dysfunction, which in turn may be used to determine whether a minimal number and duration of treatment cycles may be sufficient for treatment purposes—or extended treatment protocol needs to be implemented. The reasons for selecting an extended treatment protocol are described in greater details in my other patents and may include encountering a subject with uncompensated diabetes, hyperlipidemia, or other conditions.

In embodiments, blood flow in the limb may be measured by inflating a proximal inflatable bladder to a venous occlusion pressure—generally above central venous pressure but below diastolic blood pressure of the subject. In embodiments, the target proximal bladder pressure may be about 30, 35, 40, 45, 50, 55, 60, 65, 70, 75 or 80 mmHg. The method of measuring blood flow involves occluding venous return from the limb while allowing unrestricted arterial flow to enter the limb vasculature. Incoming blood flow will accumulate in the expanding venous system of limb vessels causing their enlargement. At first, venous blood pressure in the limb may not rise appreciably as the veins expand easily to store blood therein. As more blood flow enters the limb and accumulates in the veins, their distension will be reduced and cause a rise in venous blood pressure above the normal level—all the way up to a pressure in the proximal bladder. Depending on which limb is used for delivering remote conditioning therapy, the entire process may take anywhere between about 30 sec and about 120 sec until the venous pressure reaches the cuff pressure. Once that occurs, blood outflow will resume while the veins are fully extended.

The speed and degree of initial volume expansion of the limb when the venous pressure remains low may be used to assess blood flow thereto. Expanding limb volume may be detected using the pressure in the distal cuff. As the limb volume expands, it may cause a compression in the distal bladder which surrounds the limb tightly. A rise in distal bladder pressure may indicate the rate of blood flow in the limb—especially right after the inflation of the proximal pressure to occlude venous return. Once the rate of incoming blood flow is detected, both bladders may be deflated to low pressures around the normal central venous pressure levels of 5-10 mmHg so as to relieve previous venous congestion and allow blood to exit the limb.

FIG. 10 illustrates a process of detecting limb blood flow using a dual-bladder cuff during the period of cuff deflation. One or both bladders may be deflated to a low initial pressure of between zero and about 10 mmHg. The chart in FIG. 10 shows three pressure lines as a function of time: the top solid line is a pressure chart of the proximal inflatable bladder, the middle solid line is the venous pressure in the limb and the lower solid line is the pressure in the distal bladder. The top solid line may consist generally of three phases: initial inflation line 202 of the proximal bladder to a predetermined target level below diastolic pressure, for example 50 mmHg, selected to occlude the flow of blood out of the venous vessels of the limb but not impede the incoming blood flow in the limb arteries; steady state line 204 of maintaining the proximal bladder pressure at the target venous occlusion pressure; and the deflation line 206 when the proximal bladder is deflated to allow outflow of blood from the limb.

In response to venous occlusion by inflated proximal bladder, the limb venous vasculature expands to absorb the incoming blood flow and the venous pressure initially rises steadily as seen in the portion 222 in FIG. 10. As a large portion of the limb is under a distal bladder of the cuff, expanding volume causes a rise in the distal bladder pressure—same as portion 222 in FIG. 10. At some point, the veins become full and their further expansion involves stretching and elastic deformation, which imparts a continuously increasing pressure within the venous system. As veins resist further expansion, the distal bladder pressure curve separates from the curve of the venous pressure—the cuff is not absorbing much of the volume coming in from expanding limb tissue while the blood pressure in the veins continues to rise from the incoming arterial blood. The distal cuff pressure reaches a steady state portion 216 while the venous pressure continues to climb along the portion 214 until it reaches the level of blood pressure in the proximal bladder. Once the proximal bladder is deflated, the venous pressure drops down to initial levels—and so is the distal bladder pressure, line 218.

The slope of the initial curve portion 222 may be estimated using a fit with a straight line 220, shown as a dashed line in FIG. 10. That slope is higher if more blood flow is entering the limb and lower if less blood flow is coming into the limb. Blood flow in the limb may therefore be indirectly and non-invasively measured using the initial slope of the curve of the distal bladder pressure.

The above described method of detecting limb blood flow may be performed once or repeated from time to time during the period of cuff deflation. In embodiments, the blood flow may be performed once about 20-30 seconds after the end of the cuff inflation period. In other embodiments, it may be repeated every 10-20 sec or on another suitable schedule by dithering the pressure in the proximal bladder between the low venous pressure and the venous occlusion pressure during the first minute or so of the period of cuff deflation. Repeated blood flow measurements allow detecting a peak in limb blood flow—an increase in blood flow circulation resulting from flow-mediated dilatation. Such peak typically occurs in the first 15-45 seconds after restoring blood flow. The peak limb blood flow may then be compared to normal unrestricted blood flow in the limb, which may be obtained for example before the start of the treatment or at the end of the cuff deflation period using the same procedure. The ratio of peak flow to normal blood flow may be used to assess the health status of the subject and decide on the need for activating a standard or an extended remote conditioning treatment protocol.

If the above described ratio of flows is used for deciding on the best treatment protocol for the subject, absolute values of blood flow measurement may not be required, whereby simplifying the process. In embodiments, a ratio of peak to normal slope of increase in the distal bladder pressure may be used as a proxy for the ratio of peak to normal blood flow. The need for extended treatment may be established if that ratio is below a predetermined threshold.

It is contemplated that any embodiment discussed in this specification can be implemented with respect to any method of the invention, and vice versa. It will be also understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12, 15, 20 or 25%.

All of the devices and/or methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

I claim:

1. A device for delivery of remote ischemic conditioning treatment to a subject, said device comprising:
a cuff configured for placement over a limb of the subject, said cuff is further configured to at least partially reduce blood flow in said limb upon inflation thereof;
a controller operably connected to said cuff, said controller is configured upon activation to deliver said remote ischemic conditioning treatment by performing a plurality of remote ischemic conditioning treatment cycles, each treatment cycle comprising:
a period of cuff inflation when said controller is causing said cuff to be inflated to and maintained at or above a pressure sufficient to cause at least a partial reduction of blood flow in said limb to produce an ischemic stress therein for at least about one minute, and
a period of cuff deflation when said controller is causing said cuff to deflate so as to increase blood flow in said limb and relieve said ischemic stress,
wherein said ischemic stress is sufficient to cause said remote ischemic conditioning treatment, said controller is further configured to avoid complete occlusion of said limb by said cuff lasting more than about one minute during at least one of said treatment cycles.

2. The device as in claim 1, wherein said controller is further configured to inflate said cuff during at least a portion of said period of cuff inflation to a pressure at or below a lesser pressure of either a systolic blood pressure of said subject or a limb occlusion pressure of said subject.

3. The device as in claim 2, wherein said controller is further configured during said entire period of cuff inflation to inflate said cuff at or above a pressure sufficient to cause about ninety percent reduction of unrestricted blood flow in said limb.

4. A device for delivery of remote ischemic conditioning treatment to a subject, said device comprising:
a cuff configured for placement over a limb of the subject, said cuff is further configured to at least partially reduce blood flow in said limb upon inflation thereof;
a controller operably connected to said cuff, said controller is configured upon activation to deliver said remote ischemic conditioning treatment by performing a plurality of remote ischemic conditioning treatment cycles, each treatment cycle comprising:
a period of cuff inflation when said controller is causing said cuff to inflate to a pressure sufficient to at least partially reduce blood flow in said limb and produce an ischemic stress therein causing said remote ischemic conditioning, said period of cuff inflation lasting at least about one minute, and
a period of cuff deflation when said controller is causing said cuff to deflate and increase blood flow in said limb to relieve said ischemic stress,
wherein during at least one of said periods of cuff inflation said controller is further configured to vary pressure in said cuff so as to increase or decrease said ischemic stress in said limb.

5. The device as in claim 4, wherein said controller is further configured to vary said pressure in said cuff to cause at least one period of complete occlusion and at least one period of partial occlusion of blood flow in said limb during at least one period of cuff inflation of said treatment cycles.

6. The device as in claim 5, wherein said controller is further configured to periodically vary said cuff pressure so as to alternate complete limb occlusion with partial limb occlusion during at least one period of cuff inflation of said treatment cycles.

7. A device for delivery of remote ischemic conditioning treatment to a subject, said device comprising:
a cuff configured for placement over a limb of the subject, said cuff is further configured upon inflation to compress said limb to at least partially reduce blood flow therein;
a controller operably connected to said cuff, said controller is configured upon activation to inflate and deflate said cuff to deliver said remote ischemic conditioning treatment via performing a plurality of remote ischemic conditioning treatment cycles, each treatment cycle comprising:
a cuff inflation period wherein said cuff is inflated to a pressure sufficient to reduce blood flow in said limb and cause an ischemic stress therein to reach or exceed a predetermined ischemic stress threshold, said cuff inflation period lasting at least about one minute, and
a cuff deflation period wherein said cuff is deflated to increase blood flow in said limb and relieve said ischemic stress therein,
wherein said controller is further configured to avoid complete occlusion of blood flow in said limb by said cuff lasting more than about one minute during at least one of said treatment cycles.

8. The device as in claim 7, wherein said predetermined ischemic stress threshold is achieved by reducing blood flow in said limb below a predetermined blood flow reduction threshold.

9. The device as in claim 8, wherein said predetermined blood flow reduction threshold is about 10 percent of unrestricted blood flow in said limb.

10. The device as in claim 8, wherein said predetermined blood flow reduction threshold is about 30 ml/min.

11. The device as in claim 8, wherein said predetermined blood flow reduction threshold is about 10 ml/min per 1,000 grams of limb tissue weight.

12. The device as in claim 7, wherein said predetermined blood flow reduction is achieved by reducing cumulative limb oxygenation over the period of cuff inflation below a predetermined cumulative tissue oxygenation reduction threshold.

13. The device as in claim 12, wherein said cumulative limb oxygenation reduction threshold is about 40% of unrestricted limb oxygenation defined by unrestricted blood flow therein.

14. The device as in claim 7, wherein during at least a portion of said period of cuff inflation said cuff is inflated to at least a mean arterial pressure of said subject.

15. The device as in claim 14, wherein during at least a portion of said period of cuff inflation said cuff is inflated to a pressure exceeding said mean arterial pressure of said subject by a predetermined mean arterial pressure offset.

16. The device as in claim 7, wherein during at least a portion of said period of cuff inflation said cuff is inflated to a pressure at or below a lesser of a systolic blood pressure of said subject or a limb occlusion pressure of said subject.

17. The device as in claim 16, wherein during at least a portion of said period of cuff inflation said cuff is inflated to a pressure below said systolic blood pressure of said subject by a predetermined first systolic pressure offset.

18. The device as in claim 17, wherein said first systolic pressure offset is about 10 mmHg.

19. The device as in claim 7, wherein during said cuff deflation period, said cuff is deflated to increase blood flow above a predetermined reperfusion threshold.

20. The device as in claim 19, wherein said controller is further configured to vary cuff pressure during said period of cuff deflation so as to increase or decrease said blood flow in said limb during at least one of said treatment cycles.

21. The device as in claim 19, wherein said reperfusion threshold is defined as about 70 percent of unrestricted perfusion in said limb.

22. A device for delivery of remote ischemic conditioning treatment to a subject, said device comprising:
a cuff configured for placement over a limb of the subject, said cuff is further configured to at least partially reduce blood flow in said limb upon inflation thereof;
a controller operably connected to said cuff, said controller is configured upon activation to deliver said remote ischemic conditioning treatment by performing a plurality of remote ischemic conditioning treatment cycles, each treatment cycle comprising:
a period of cuff inflation when said controller is causing said cuff to be inflated to and maintained at or above a pressure sufficient to cause at least a partial reduction of blood flow in said limb to produce an ischemic stress therein for at least about one minute, and
a period of cuff deflation when said controller is causing said cuff to deflate so as to increase blood flow in said limb and relieve said ischemic stress,
wherein said ischemic stress is sufficient to cause said remote ischemic conditioning treatment, said controller is further configured on a predetermined schedule to vary cuff pressure during at least one period of cuff inflation so as to alternate between partial occlusion and complete occlusion of said blood flow in said limb during at least one of said treatment cycles.

* * * * *